United States Patent [19]
Bueche et al.

[11] Patent Number: 5,982,285
[45] Date of Patent: Nov. 9, 1999

[54] COMPLIANCE MONITORING SYSTEM

[76] Inventors: Kenneth M. Bueche, 213 St. Cloud, Friendswood, Tex. 77546; Robin E. Bowen, 6408 W. 66th St., Overland Park, Kans. 66202; Robert W. Schroeder, 5930 McGee, Kansas City, Mo. 64113; David W. Peterson, 14720 W. 80th St., Lenexa, Kans. 66215

[21] Appl. No.: 09/078,835

[22] Filed: May 14, 1998

[51] Int. Cl.$^6$ ..................................................... G08B 23/00
[52] U.S. Cl. .................................. 340/573.1; 340/686.1; 340/604; 602/64
[58] Field of Search .................................... 340/573, 673, 340/666, 665, 686.1, 600, 604, 573.1, 573.4, 686.4; 602/64

[56] References Cited

U.S. PATENT DOCUMENTS

| | | | |
|---|---|---|---|
| 4,536,755 | 8/1985 | Holzgang et al. | 340/573 |
| 4,608,998 | 9/1986 | Murdock | 340/573 |
| 4,972,177 | 11/1990 | Nolan | 340/573 |
| 5,038,137 | 8/1991 | Lloyd | 340/573 |
| 5,177,469 | 1/1993 | Igarashi et al. | 340/573 |
| 5,424,720 | 6/1995 | Kirkpatrick | 340/585 |
| 5,469,861 | 11/1995 | Piscopo et al. | 340/573 |
| 5,528,228 | 6/1996 | Wilk | 340/686 |
| 5,543,780 | 8/1996 | McAuley et al. | 340/573 |
| 5,633,627 | 5/1997 | Newham | 340/573 |
| 5,745,037 | 4/1998 | Gurthrie et al. | 340/573 |
| 5,751,214 | 5/1998 | Cowley et al. | 340/573 |
| 5,754,121 | 5/1998 | Ward et al. | 340/573 |
| 5,877,696 | 3/1999 | Powell | 340/825.32 |

OTHER PUBLICATIONS

Handheld Datalogging System Model OM–550—p. S–135.
Microprocessor–Based Portable Datalogger pp. S–131, 132, 133.
Instrumented Sensor Technology—web page http://www.isthq.com/museum.html.
Portable Intelligent Datalogger—pp. S–129–130.
Desicare, Inc. Humidity Indicating Cards—web page—http://ww.desiccare.com/humcards.htm.
Shockwatch—global Solutions for Damage Prevention—web page—http://www.shockwatch.com/index.html.
Shockwatch Products: Heatwatch—http://www.shockwatch.com/products/heatwatch.html (2) pages.
Shockwatch: Packaging Products—web page—http://www.shockwatch.com/products/packaging/html.
Shockwatch: products—web page—http://www.shockwatch.com/products.html.
Shockwatch: Intermodal Products—web page—http://www.shockwatch.com/products/rta.html.
Shockwatch: Data Reporting Accessories—web page—http://www.shockwatch.com/products/access.html.

*Primary Examiner*—Daniel J. Wu
*Assistant Examiner*—Anh La
*Attorney, Agent, or Firm*—Hovey, Williams, Timmons & Collins

[57] ABSTRACT

A compliance monitoring apparatus (10) includes sensors (70, 72, 74, 76) for sensing specified conditions such as temperature and impact, and a signal processor (26) for storing sensor data and concurrent time data for subsequent analysis. The invention finds utility in monitoring compliance with a prescribed mode of a person wearing an appliance such as a splint (12), and for monitoring the conditions experienced by a package (100) during shipment.

9 Claims, 2 Drawing Sheets

COMPLIANCE MONITORING SYSTEM

RELATED APPLICATIONS

Not applicable.

FEDERALLY SPONSORED RESEARCH OR DEVELOPMENT

Not applicable.

MICROFICHE APPENDIX

Not applicable.

BACKGROUND OF THE INVENTION

1. Field of the Invention

The invention deals with the field of compliance monitoring such as compliance with a prescribed mode for wearing a medical appliance, or compliance with specified shipping conditions for a package, for example. More particularly, the invention is concerned with a monitoring apparatus having at least one sensor for sensing a specified condition such as temperature or impact, and a signal processor for storing sensor data and concurrent time data for subsequent analysis along with being small, disposable, portable, and providing a permanent record of events.

2. Description of the Prior Art

In the treatment of certain medical conditions, a patient may be instructed to wear a medical appliance according to a prescribed mode. For example, a patient, having undergone surgery for carpal tunnel syndrome, may need to wear a detachable splint immobilizing the wrist joint. However, some patients may remove the splint prematurely because of the inconvenience. If problems develop as a result, it is often difficult to diagnose the reason because the attending physician is not aware that the splint has not been worn as prescribed.

In the field of shipping, some goods must be shipped under specific conditions. For example, some perishable products must be shipped within a certain temperature range and fragile products must be handled carefully without dropping or other sudden impact. However, if damaged products are received there is usually no way to determine if or when the shipping instructions were violated.

SUMMARY OF THE INVENTION

The present invention solves the prior art problems mentioned above and presents a distinct advance in the state of the art. In particular, the monitoring apparatus hereof provides a date and time stamped record of selected conditions concerning the wearing of an appliance or a shipment of goods, for example.

The preferred embodiment includes at least one sensor for sensing a specified condition coupled with a signal processor for storing sensor data along with concurrent time data. In one embodiment, the sensed condition is indicative of whether a person is wearing a prescribed appliance such as a splint. Sensors such as temperature and light sensors are coupled with the interior of the splint. The presence of body temperature and the absence of light indicate that the splint is being worn and converse indicate that the splint is not being worn. Sensor data representative of these conditions are stored along with concurrent time data in memory for subsequent downloading and analysis in a personal computer.

In another embodiment, the signal processor is enclosed by a housing with sensors therein for sensing shipping conditions within a package. These conditions might include temperature and impact. The apparatus is shipped in the package along with the goods. Upon receipt, the sensor and time data can be downloaded and analyzed in a personal computer to determine compliance with the shipping instructions and kept for permanent records. Other preferred aspects of the invention are disclosed herein.

DETAILED DESCRIPTION OF THE PREFERRED EMBODIMENT

Figure 3:
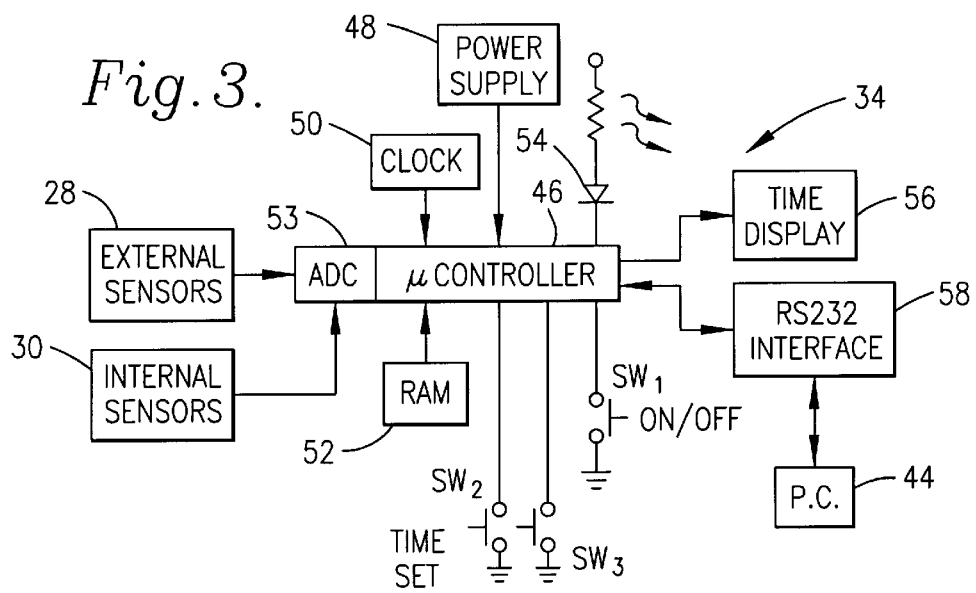
FIG. 3 is an electrical block diagram of the apparatus of FIG. 1.
Figure 2:
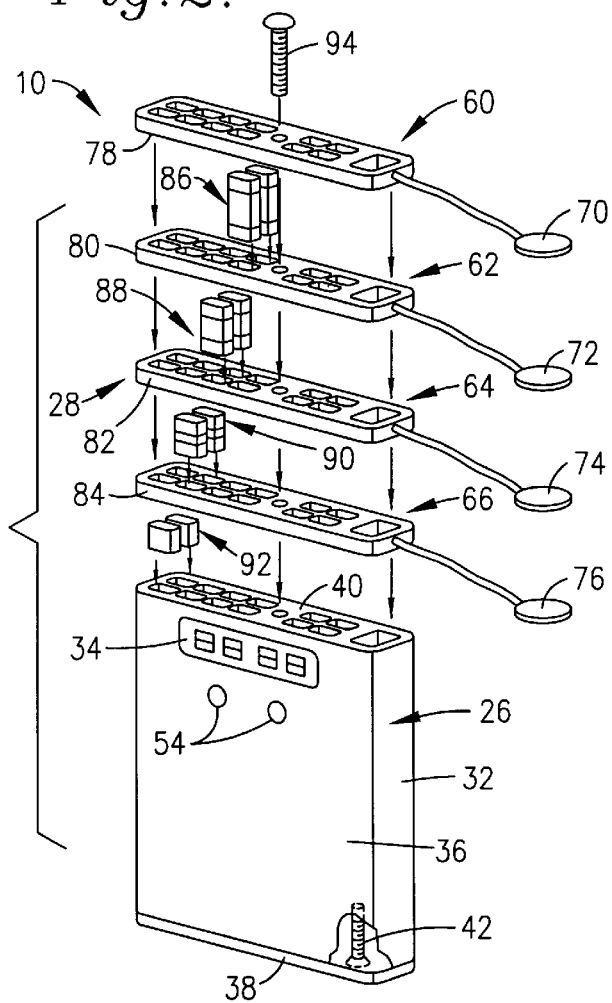
FIG. 2 is an exploded, pictorial view of the apparatus of FIG. 1.
Figure 1:
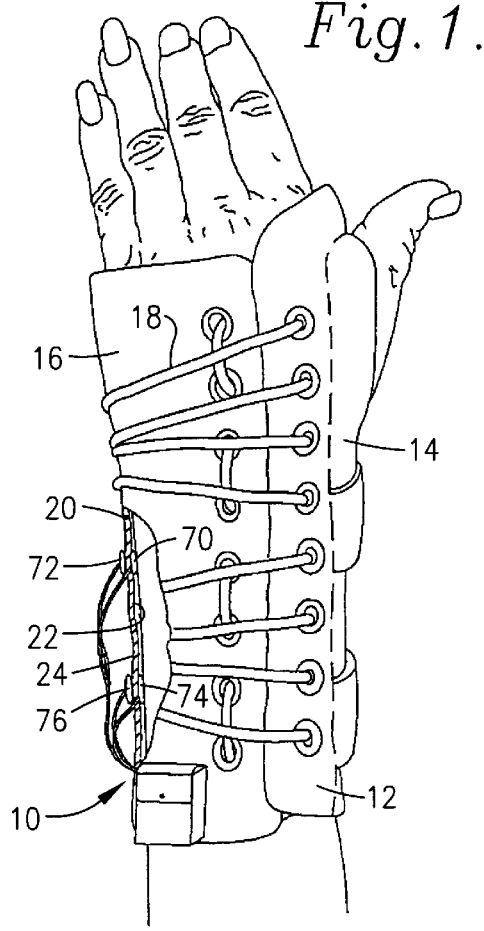
FIG. 1 is a pictorial view of one embodiment of the preferred compliance monitoring apparatus in accordance with the present invention shown in use with a splint with portions cut away for clarity of illustration and shown being worn by a person.

FIG. 1 illustrates a first embodiment of the preferred compliance monitoring apparatus 10 of the present invention shown in use with splint 12 being worn by a person. Splint 12 includes two sections 14 and 16 held together by laces 18. Section 16 includes wall 20 presenting inner surface 22 adjacent the skin of the person and opposed outer surface 24. Referring also to FIGS. 2 and 3, apparatus 10 includes signal processor 26, external sensor assembly 28 and internal sensors 30.

Signal processor 26 includes housing 32 enclosing signal processing circuit 34. Housing 32 is preferably composed of high impact synthetic resin material and includes side walls 36, removable end wall 38, and connection face 40. A plurality of screws such as screw 42 couple end wall 38 with side walls 36 and when removed, allow access to the interior of housing 32 and thereby access to circuit 34. As will be appreciated, screw 42 or end wall 38 can be sealed to provide evidence of tampering. Connection face 40 provides connections to external sensor assembly 28 and to personal computer 44 as explained further herein.

Signal processing circuit 34 includes microcontroller 46 connected to power supply 48, clock 50 and non-volatile random access memory (RAM) 52. Microcontroller 46 receives inputs from analog-to-digital converter (ADC) 53, on/off switch SW1, and clock set switches SW2 and SW3. Microcontroller 46 provides outputs to light emitting diode (LED) 54 and to time display 56, and is connected with RS232 serial interface 58 for two-way data transfer with PC 44.

External sensor assembly 28 includes sensor modules 60, 62, 64 and 66. Modules 60–66 include respective temperature sensors 70, 72 and light sensors 74 and 76 connected by wire pairs to respective mounting blocks 78, 80, 82 and 84.

As illustrated in FIG. 2, mounting blocks 78–84 are configured to fit one atop the other with block 84 positioned against connection face 40 of housing 32. Screw 94 holds modules 60–66 in position coupled with housing 32.

Respective pairs of connection pins 86, 88, 90 and 92 fit through the modules as illustrated to align modules and to provide the electrical connection between sensors 70–76 and ADC 53.

The configuration of apparatus 10 enables convenient replacement of modules or the connection of more or fewer modules as needed. It will be appreciated that there are a wide variety of other types of sensors that can be used for measuring particular conditions as needed. These include sensors for moisture, motion, position, impact and skin resistivity, for example.

Referring to FIG. 1, temperature sensor 70 is positioned in splint wall 20 flush with inner surface 22 to sense body heat, and temperature sensor 72 is positioned on the opposite side of wall 20 flush with outer surface 24 to sense ambient temperature. Similarly, light sensor 74 is positioned flush with inner surface 22, and light sensor 76 is positioned flush with outer surface 24.

By providing two types of sensors, and two sensors of each type, the accuracy of apparatus 10 is enhanced. For example, inner temperature sensor 70 adjacent the wearer's skin may indicate body temperature but such would not indicate that splint 12 is being worn if ambient temperature is also the same as normal body temperature, which might occur outdoors in warm weather. However, outer light sensor 76 would indicate the presence of light and inner light sensor 74 would indicate darkness within splint 12, thereby confirming that the person is wearing splint 12.

In another circumstance, both light sensors 74, 76 might indicate darkness such as when the person is sleeping, but temperature sensors 70 and 72 would indicate a differential with sensor 70 being at body temperature. This would confirm that splint 12 is being worn. Conversely, if both temperature sensors 70, 72 are at the same temperature, and light sensors 74, 76 indicate the same light level, then such would indicate that splint 12 is not being worn.

Internal sensors 30 can include any of the types discussed above. In the embodiment of FIG. 1, for example, internal sensors 30 could include a motion sensor for providing confirming information that the splint is being worn. As another example, internal sensors 30 could include a temperature sensor for indicating ambient temperature rather than having an external sensor for this purpose.

FIG. 1 illustrates one example of the use of apparatus 10 with splint 12 on a person's arm 96. In preparation, screws 42 are removed and end wall 38 removed to provide access to time set switches SW2 and SW3 and also to time display 56. Switches SW2 and SW3 are used to set the time of day and date as shown by display 56. These settings determine the time-of-day data stored in association with sensor data discussed further herein. End wall 38 and screws 42 are then replaced and sealed if desired. Also as part of the set up routine, PC 44 is connected to signal processor 26 to initialize the program stored in microcontroller 46 and to initialize RAM 52.

Splint 12 is then positioned on the patient's arm 96. With splint 12 in place, switch SW1 is pressed to activate signal processor 26 including microcontroller 46.

In operation, signal processor 26 samples the inputs from external sensors 70–76 and internal sensors 30. These sensors provide analog sensor signals that are converted by ADC 53 to digital sensor signals received by microcontroller 46.

In response to the receipt of the digital sensor signals, microcontroller 46 stores sensor data representative thereof in RAM 52. Additionally, microcontroller 46 stores concurrent time-of-day data received from clock 50 in RAM 52 in association with the sensor data. In the preferred embodiment, the time-of-day data also includes the calendar date. It is preferred that sampling rate and the capacity of RAM 52 be such so that six months' of data can be stored in RAM 52.

After the prescribed time period, signal processor 26 is connected with PC 44. The data from RAM 52 is downloaded to PC 44 which analyzes the data to determine the time frames during which splint 12 was worn and not worn. This data can then be displayed in a conventional manner to illustrate when the splint was worn and when it was not.

With this information, it can be determined whether the patient complied with the prescribed mode of treatment. For example, if the patient's condition has not improved and the splint has not been worn as prescribed, this can provide valuable information to the person making the diagnosis. similarly, if the patient's condition has not improved but the patient has complied by wearing the splint as prescribed, then a different diagnosis and treatment regiment may result.

Figure 4:
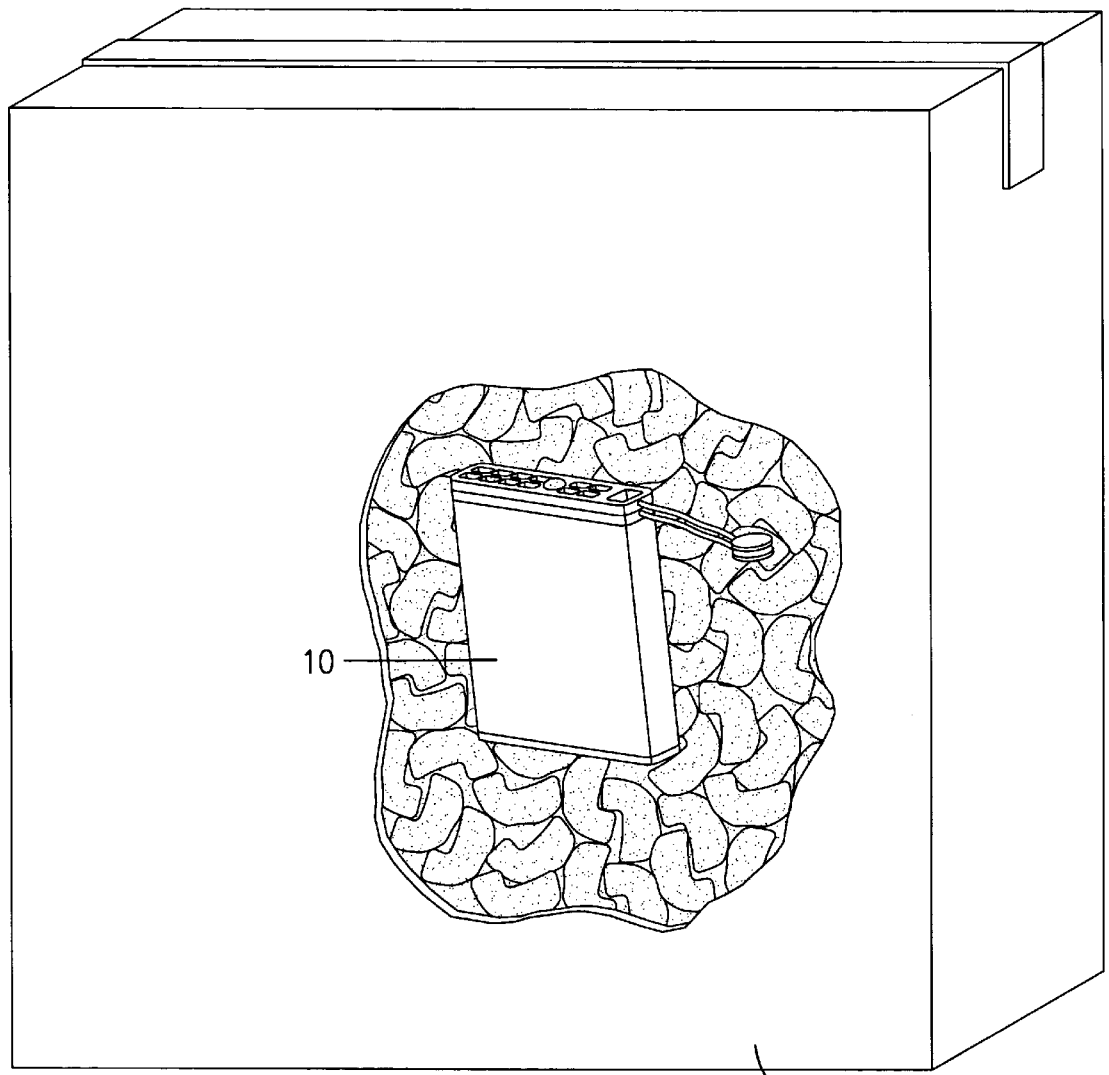
FIG. 4 is a pictorial view of another embodiment of the preferred compliance monitoring apparatus in accordance with the present invention shown positioned in a package with portions cut away for clarity of illustration.

FIG. 4 illustrates another embodiment of the present invention. Specifically, FIG. 4 shows apparatus 10 positioned within package 100 for monitoring the shipping conditions experienced by package 100. The specific conditions monitored depend upon the nature of the goods being shipped and the mode of transport.

For example, if the goods are temperature sensitive, then either internal or external temperature sensors would be used with apparatus 10. If the goods are received in less than expected condition, the sensor and time data can be downloaded and analyzed on PC 44 to determine if the goods experienced temperatures outside the prescribed range during shipment. This can be important to demonstrate for insurance recovery or the like. In other circumstances, the goods might be fragile in which case the sensors would include an impact sensor, that is, accelerometer. Data from this type of sensor would indicate whether the package had been dropped, for example. As a further example, it might be important that the package remain upright during shipment. In this case, the sensors could include a position sensor to indicate the orientation of the package during shipment. Other sensors might include humidity and moisture, for example.

Figure 5:
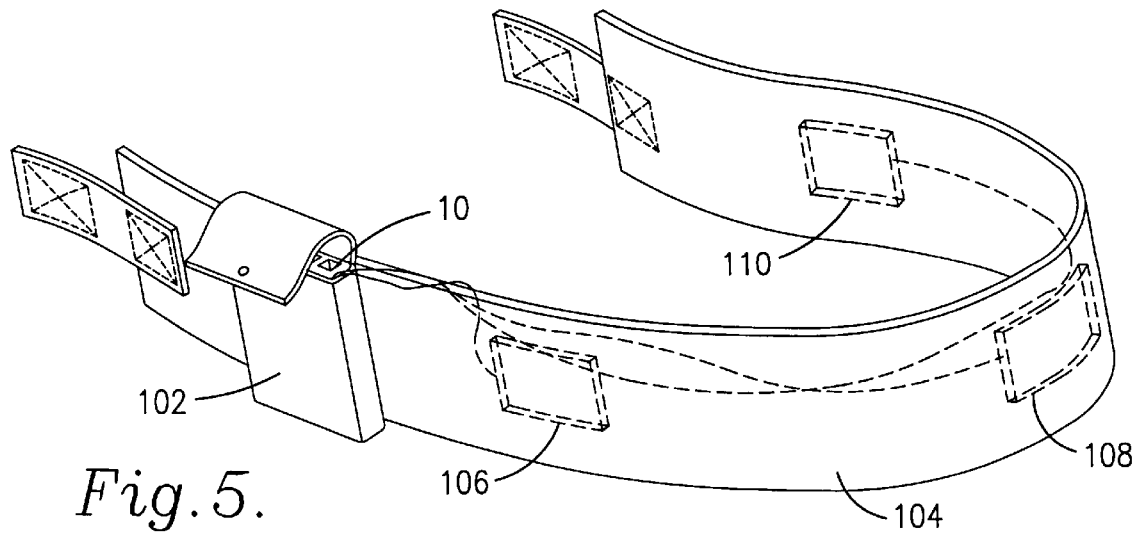
FIG. 5 is a pictorial view of another embodiment of the preferred compliance monitoring apparatus in accordance with the present invention.

FIG. 5 illustrates still another embodiment of the present invention. In particular, FIG. 5 shows apparatus 10 received in pouch 102 attached to the outboard face of belt 104 with three sensors 106, 108 and 110 in the nature of pressure switches attached to the inboard face of belt 104 and spaced therealong. Belt 104 is configured to be worn by a bedridden patient with sensors 106–110 indicating the position of the patient, that is, whether the patient is lying on one side, the other side or on the patient's back. The corresponding sensor data stored in RAM 52 provides a record of whether the patient has been turned frequently enough to avoid bed sores, for example.

Those skilled in the art will appreciate that the present invention encompasses many variations in the embodiments described herein. Having described these embodiments, the following is claimed as new and desired to be secured by Letters Patent:

What is claimed is:

1. A compliance monitoring apparatus for monitoring the amount of time a person wears a medical appliance according to a prescribed mode, said apparatus comprising:

sensor means, including means for coupling with the medical appliance, for sensing a condition indicative of whether the person is wearing the medical appliance and for producing sensor signals representative thereof; and signal processing means, including a data storage and retrieval device and means for producing time data representative of the time of day, for receiving said sensor signals and responsive thereto for storing, in said data storage and retrieval device, sensor data representative thereof and concurrent time data in association therewith, said sensor data and concurrent time data cooperatively representing the time frames during which the medical appliance was worn by the person so that the amount of time the person wears the medical appliance can be determined for monitoring whether the person has worn the medical appliance according to the prescribed mode.

2. The apparatus as set forth in claim 1, further including analysis means for analyzing said sensor data and time data for determining said time frames and comparing said time frames to a prescribed mode to determine whether the person has worn the medical appliance according to the prescribed mode.

3. The apparatus as set forth in claim 2, said analysis means including a personal computer including a computer program stored therein on computer readable memory for operating said personal computer to perform said analyzing.

4. The apparatus as set forth in claim 1, said sensor means including at least one of a moisture sensor, motion sensor and skin contact sensor for sensing the respective conditions of moisture on a person's skin adjacent the medical appliance, motion of the medical appliance during wearing, and skin resistivity.

5. The apparatus as set forth in claim 4, said sensor means including a plurality of said sensors.

6. The apparatus as set forth in claim 1, said signal processing means including a microcontroller.

7. The apparatus as set forth in claim 1, said data storage and retrieval device including a nonvolatile random access memory.

8. The apparatus as set forth in claim 1, said time data including the date.

9. The apparatus as set forth in claim 1, the medical appliance including a splint, said sensor means including means for sensing a condition indicative of whether the person is wearing the splint.

* * * * *